United States Patent [19]
Yarrow

[11] Patent Number: 4,499,613
[45] Date of Patent: Feb. 19, 1985

[54] ANKLE JOINT AND COUPLING FOR ARTIFICIAL LIMBS
[76] Inventor: Harry A. Yarrow, 135 S. Sparks St., Burbank, Calif. 91506
[21] Appl. No.: 471,274
[22] Filed: Mar. 1, 1983
[51] Int. Cl.³ ............................................. A61F 1/04
[52] U.S. Cl. ............................................ 3/31; 3/30; 3/6
[58] Field of Search ................. 3/2, 22, 23, 30, 31, 3/32, 33, 34, 35, 6, 61, 7

[56] References Cited
U.S. PATENT DOCUMENTS

| 608,812 | 8/1898 | Weller | 3/32 |
| 1,368,348 | 2/1921 | Moore | 3/35 |
| 2,617,115 | 11/1952 | Ellery | 3/35 |

FOREIGN PATENT DOCUMENTS 1010648  6/1952  France ........................ 3/6

Primary Examiner—Richard J. Apley
Assistant Examiner—David J. Isabella
Attorney, Agent, or Firm—Harvey B. Jacobson

[57] ABSTRACT

An ankle joint enabling an amputee to walk more naturally with better balance and security in which an ankle or like joint is constructed with broad circumferential surfaces so that it will resemble the action of the human ankle when walking. The ankle joint is composed of one cup-shaped member attached to the bottom of the leg sliding over another cup-shaped member attached to the top of a foot. A third cup-shaped member fits over the first cup-shaped member and a bolt extends through the foot and the cup-shaped members to secure them in assembled relation. Lateral sides of the cups are essentially vertically straight preventing any rotary movement about a vertical axis and the bolt has a pivot joint enabling lateral movement of the foot about a front to rear axis. A resilient cushion is mounted on the upper end of the bolt and engages a cavity in the lower end of the leg to cushion and control the articulate movement of the foot in relation to the leg. Also, an adjustable ankle stop is mounted on a forward extension on the leg to engage the foot to provide an effective stop which can be adjusted to compensate for shoes having different heel height.

9 Claims, 5 Drawing Figures

ANKLE JOINT AND COUPLING FOR ARTIFICIAL LIMBS

BACKGROUND OF THE INVENTION

1. Field of the Invention

The present invention relates to an ankle joint and coupling arrangement for artificial limbs designed to enable an amputee to use the artificial limbs with greater facility, and more particularly to enable the amputee to walk more naturally with better balance and more security. The ankle joint of the present invention has a broad circumferential surface around a transverse axis about which movement is obtained which resembles the action of the human ankle. The ankle joint of this invention includes an inverted cup-shaped or curvilinear contoured member attached to the bottom of the leg member for sliding over another inverted cup-shaped member or lateral rocker member engaging the top of the foot which has a longitudinally oriented groove having an arcuate bottom surface. The parts are interconnected by a bolt extending therethrough with the bolt including a lateral motion joint at the upper surface of the foot member.

Also, the invention relates to a combination of an ankle joint and coupling for leg and foot members and in which there is a variable ankle stop for variably adjusting the limits of movement between the leg member and the foot member to accommodate any size shoe, shoe heel, tennis shoes, and the like. The variable ankle stop consists of a bolt member fastened to the leg member and having its extension portion limiting the articulated movement of the leg member with the foot, so that by using simple tools, the user may vary the stop position.

2. Description of the Prior Art

Various prior U.S. patents relate to coupling and joint elements for artificial limbs, and of interest to the present invention are the following U.S. patents:

U.S. Pat. Nos.: 433,497—Aug. 5, 1890—Swank
710,966—Oct. 14, 1902—Peer
975,439—Nov. 15, 1910—Lawrence
1,091,115—Mar. 24, 1914—Blon
1,368,348—Feb. 15, 1921—Moore
2,439,195—Apr. 6, 1948—Witmyer et al
4,089,072—May 15, 1978—Glabiszewski.

The patent to Witmyer et al discloses a series of cup elements for artificial limb joint members which function in a manner providing articulated movement between the members. The other enclosed patents disclose various joints and components used with artificial limbs and none of these patents provide disclosure of all of the specifics of the present invention in such a way as to bear upon the patentability of any claim of the present invention.

SUMMARY OF THE INVENTION

An object of the present invention is to provide an ankle joint for artificial limbs that enables an amputee to walk more naturally with better balance and with more security by providing transversely flat and arcuate longitudinal surfaces in sliding engagement to more closely resemble the action of the human ankle joint. The ankle joint of the present invention is composed of an inverted cup attached to and received within a recess in a leg member in sliding engagement with an underlying inverted cup member and an overlying cup member with a bolt extending through the foot and cup members to retain the components in assembled relation.

Another object of the invention is to provide an ankle joint for artificial limbs in accordance with the preceding object in which the bolt is provided with a pivot joint which enables lateral movement between the leg and foot about a front to rear axis which is generally perpendicular to the transverse axis defined by the cup members.

A further object of the present invention is to provide an ankle joint and coupling for artificial limbs which includes an adjustable stop arrangement that compensates for differences in shoe sizes, shoe heel configurations and other dimensional variations. The stop for the artificial limb serve the same purpose as the achilles tendon of the foot. Whereas the muscles adjust the relative positions of the foot to the leg when heel heights vary, the artificial limbs of the prior art do not have this full capability, but by means of the use of the present invention, when an amputee using the present invention has a desired shoe fitted to the foot member, then the stop assembly may be adjusted for that heel height by adjusting the stop so that the leg maintains its perpendicular orientation or position relative to the foot member or the ground. The amputee need not always wear the same shoe with the same heel height since the stop can be readjusted when a shoe with a different heel height is placed on the foot member.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
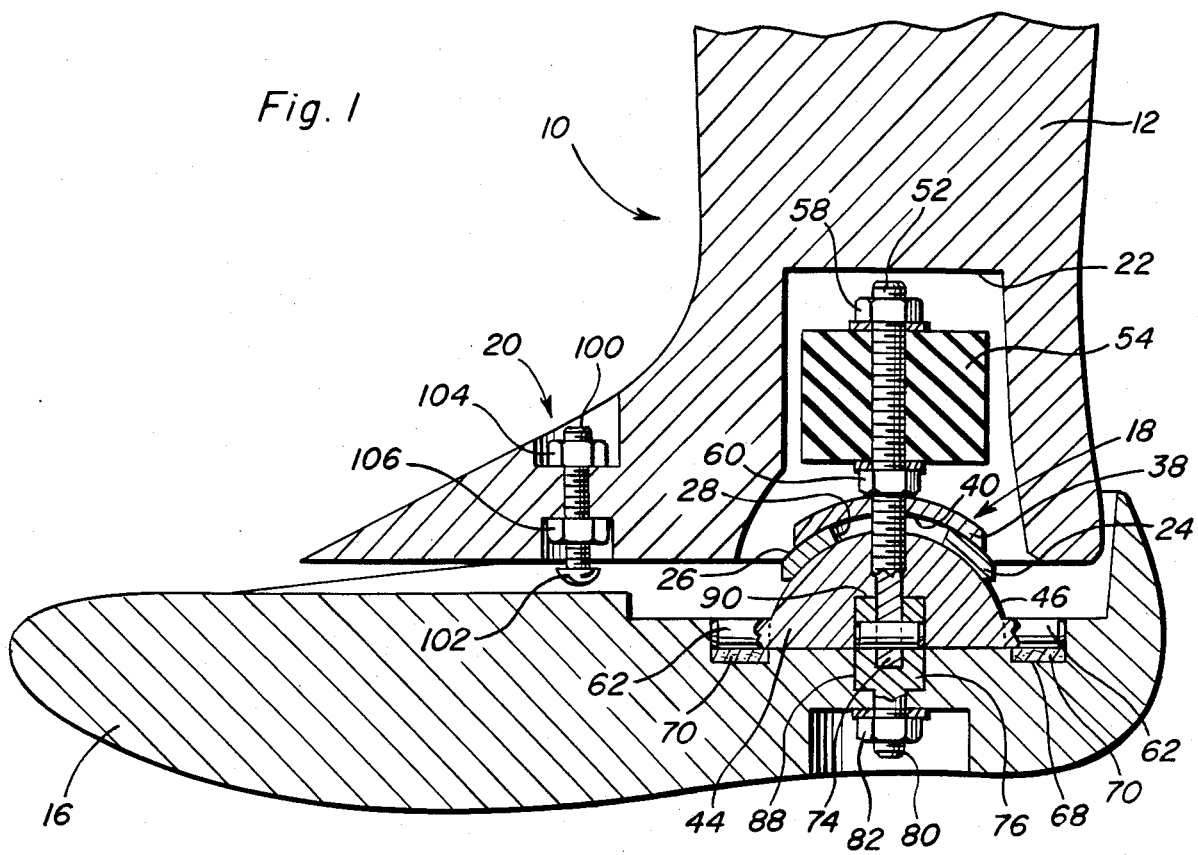
FIG. 1 is a longitudinal sectional view of an ankle joint and coupling for artificial limbs according to the present invention.

Referring now to the drawings, there is shown an ankle joint and coupling arrangement 10 for artificial limbs including a lower extremity of a leg member 12 and a foot member 16 with the leg member 12 and foot member 16 being connected by an ankle joint generally designated by reference numeral 18 and an adjustable stop arrangement 20 limits the relative movement between the leg member 12 and foot member 16 in one direction about a transverse axis. The lower end of the leg member 12 includes a cavity 22 preferably square in cross-sectional configuration which is shaped and adapted to receive a portion of the ankle joint 18.

Figure 2:
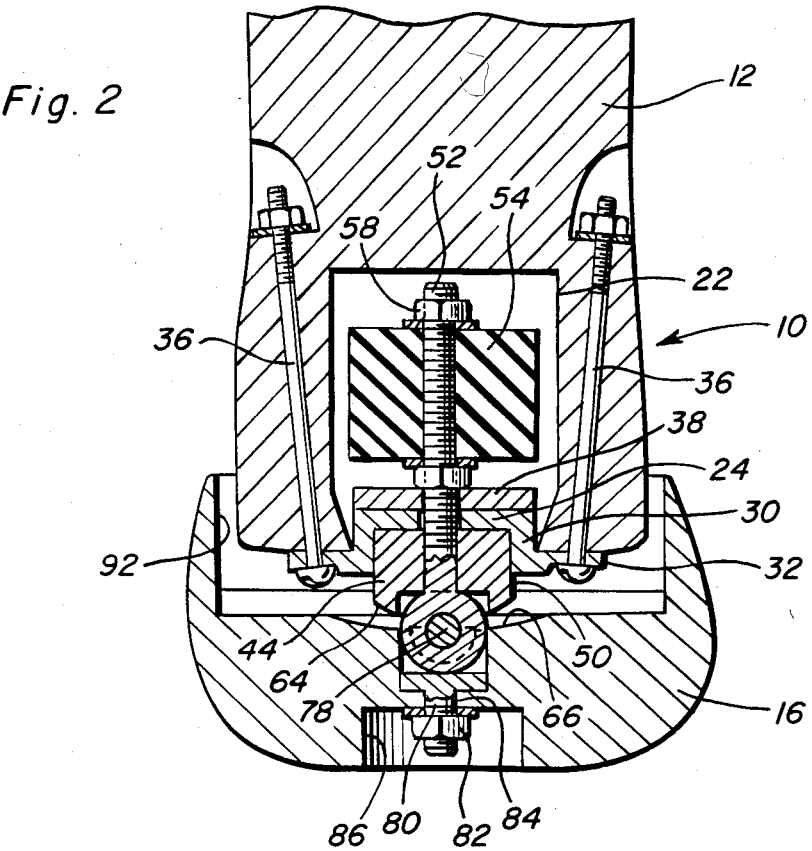
FIG. 2 is a transverse sectional view taken along the connecting bolt.
Figure 3:
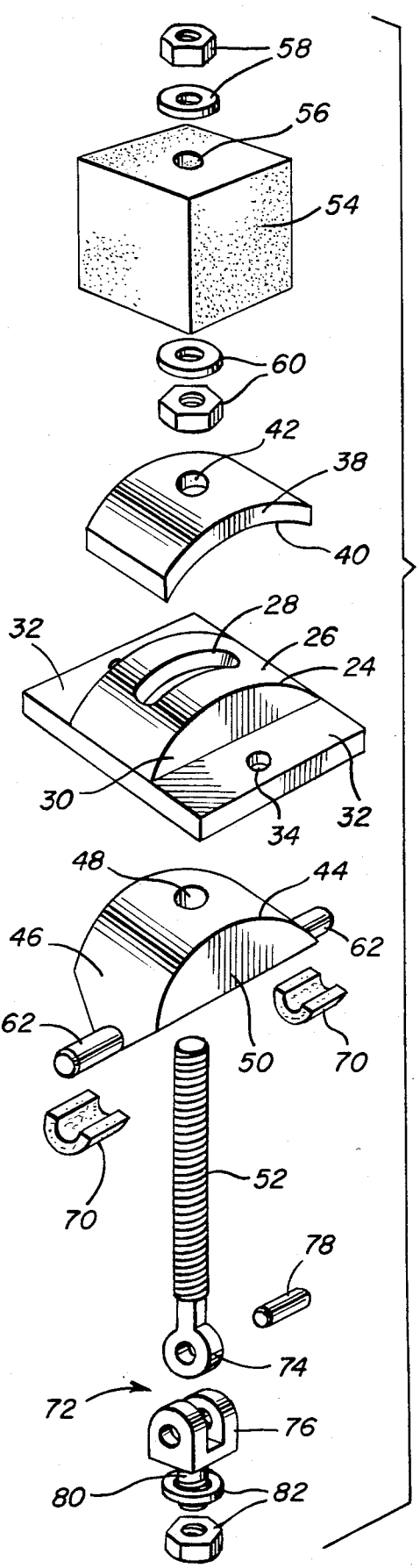
FIG. 3 is an exploded perspective view of various components of the ankle joint and coupling.

FIG. 3 illustrates the components of the ankle joint 18 in the relationship in which they are assembled and which includes an inverted cup-shaped member 24 that includes an arcuately curved upper surface 26 that is transversely flat or straight for a substantial distance as illustrated in FIG. 3 with the undersurface of the cup-shaped member being correspondingly arcuately curved. An arcuate slot 28 is formed in the curved surface 26 and extends for a substantial distance along the center of the arcuately curved surface 26. The cup-shaped member 24 includes side walls or members 30 which are parallel to each other and substantially straight with the side members generally closing the ends of the arcuate central portion of the cup-shaped member 24. Projecting laterally from the bottom edge of each side member 30 is a flange 32 having an aperture or apertures 34 therein by which the cup-shaped member may be secured to the bottom surface of the leg member 12 by suitable fastening members such as bolts 36 or other suitable fastener members with the hollow arcuate portion of the cup-shaped member 24 being disposed in the lower portion of the cavity 22 as illustrated in FIG. 2. Positioned in overlying and sliding engagement with the arcuate surface 26 of the cup-shaped member 24 is an overlying cup-shaped member 38 in the form of an arcuate plate having an arcuate bottom surface 40 conforming in curvature with the surface 26 and in sliding engagement therewith. The upper surface of the cup-shaped member 38 may also be arcuate and a central aperture 42 extends through the cup-shaped member 38 in alignment with the arcuate slot 28 in the cup-shaped member 24. Positioned in underlying engagement with the cup-shaped member 24 in a rocker member 44 having an arcuate upper surface 46 with the same degree of curvature as the lower surface of the cup-shaped member 24 and in sliding engagement therewith with the rocker member 44 being generally an inverted cup-shaped member and provided with a centrally disposed aperture 48 extending therethrough and in alignment with the slot 28. The rocker member 44 is provided with substantially parallel flat side walls 50 which are received between and closely engage the inner surface of the parallel side members 30 of the cup-shaped member 24 so that, in effect, the upper portion of the rocker member 44 is received within the cavity or recess formed in the lower surface of the cup-shaped member 24 with the engagement of the side walls 50 with the side members 30 preventing relative movement about the axis of the aperture 48 while engagement of the arcuate surfaces enables relative movement about a transverse axis perpendicular to the axis of the aperture 48.

An elongated threaded bolt 52 interconnects the leg member 12 and foot member 16 in a manner described hereinafter and is received vertically through the aperture 48, slot 28 and aperture 42 as illustrated in FIGS. 1 and 2 with the upper end portion of the bolt 52 extending through a block of resilient material 54 having a central aperture 56 therein with the bolt being provided with a nut and washer and assembly 58 on the upper end thereof a nut and washer assembly 60 thereon in underlying relation to the block of resilient material 54. The nut 60 adjustably engages the upper surface of the cup-shaped member 38 and the surface of the cup-shaped member 38 surrounding the aperture 42 may be built up to provide a flat surface or an adapter washer may be positioned therebetween so that the nut can be adjustably tightened to retain the members in assembled relation with the frictional engagement between the arcuate surfaces of the components being varied by adjusting the nut 60 downwardy and upwardly on the bolt 52. The block of resilient material 54 is retained on the upper end of the bolt 52 by the nut and washer assembly 58 with adjustment thereof enabling some compression of the block of resilient material 54 to vary the relationship of the periphery of the block 54 to the cavity 22 with the purpose of the resilient block 54 being to engage the front and rear surfaces of the cavity 22 during normal walking to cushion and progressively resist pivotal movement about a transverse axis to more closely simulate the action of the ankle joint of a human being.

The lower surface of the rocker member 44 is provided with a pair of rocker shafts 62 which extend forwardly and rearwardly from the rocker member with the lower surface thereof being generally flush with the lower surface of the rocker member 44 which is arcuately curved as at 64 with this surface being received in a cavity or recess 66 in the upper surface of the foot member 16. The recess 66 includes a pair of longitudinally aligned channels or grooves 68 in each end portion thereof with each groove 68 including a liner 70 of leather or the like which receives and cushions the rocker shafts 62. Thus, the engagement of the rocker shafts 62 with the lined grooves forms a front to rear pivot axis between the foot member 16 and the leg member 12 while the arcuate surfaces 46, 26 and 40 form a transverse pivotal axis between the foot member 16 and leg member 12. The lower end of the bolt 52 includes a joint generally designated by numeral 72 which enables lateral pivotal movement of the foot member with the joint 72 including an eye 74 on the lower end of the bolt 52 which is pivotally connected to a U-shaped clevis 76 by a pin 78. Depending from the clevis 76 is a threaded bolt segment 80 having a nut and washer assembly 82 threaded thereon. The bolt segment 80 extends through an aperture 84 in the foot member 16 and the nut and washer assembly are received in a recess 86 in the bottom of the foot member as illustrated in FIGS. 1 and 2. The pivotal joint 72 is received in a recess 88 communicating with the recess 66 as illustrated in FIGS. 1 and 2 with a portion of the joint 72 also being received in a recess 90 in the bottom of the rocker member 44. As illustrated in FIGS. 1 and 2, the pin 78 which connects the eye 74 and clevis 76 is parallel with and in alignment with the rocker shafts 62 so that the pivotal connection between the bolt 52 and the bolt segment 80 is in alignment with and forms a continuation of the pivotal axis defined by the rocker shafts 62 thereby defining a front to rear pivotal axis between the foot member 16 and the leg member 12 with the leather lining 70 serving as a cushioning arrangement and also a friction arrangement to prevent free lateral movement of the foot member. This construction enables the foot member to incline about a front to rear axis in the event the foot member is brought downwardly into engagement with an inclined supporting surface thereby further resembling the action of a human ankle joint. The recess 66 in the upper surface of the foot member includes rear and sidewall portions 92 which telescope over the lower portion of the leg member 12 and the sidewall portions would limit the lateral pivotal movement of the foot member 16 in relation to the leg member 12. Also, to facilitate assembly, the bolt segment 80 may be threaded into the clevis 76 and the bolt 52 may include a threaded connection with the eye 74. Other types of pivotal connections may be employed in lieu of that specifically illustrated with the pivotal connection enabling lateral movement of the foot member 16 about a front to rear axis with this connection avoiding any looseness which introduces a feeling of insecurity and preventing free lateral swinging movement of the foot which would also introduce a feeling of insecurity.

FIG. 1 illustrates the adjustable stop assembly 20 in a forward portion of the leg member 12 which comprises a bolt 100 having its head 102 projecting or extending beyond the lower surface of leg member 12 so that the head 102 may engage the upper surface of the foot member 16 as the foot member articulates, respectively with respect to the leg member 12 about the ankle joint 10 with the bolt 100 having adjustable lock nuts 104 and 106 thereon to vary the position of bolt head 102.

Figure 4:
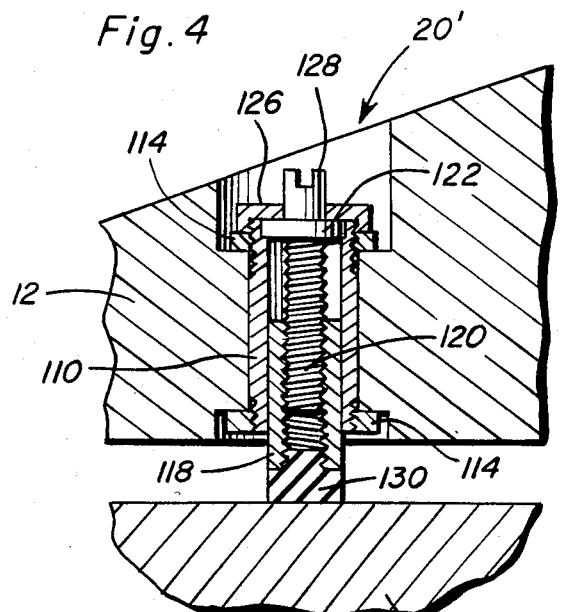
FIG. 4 is a vertical sectional view of an alternative ankle stop to that shown in FIG. 1.
Figure 5:
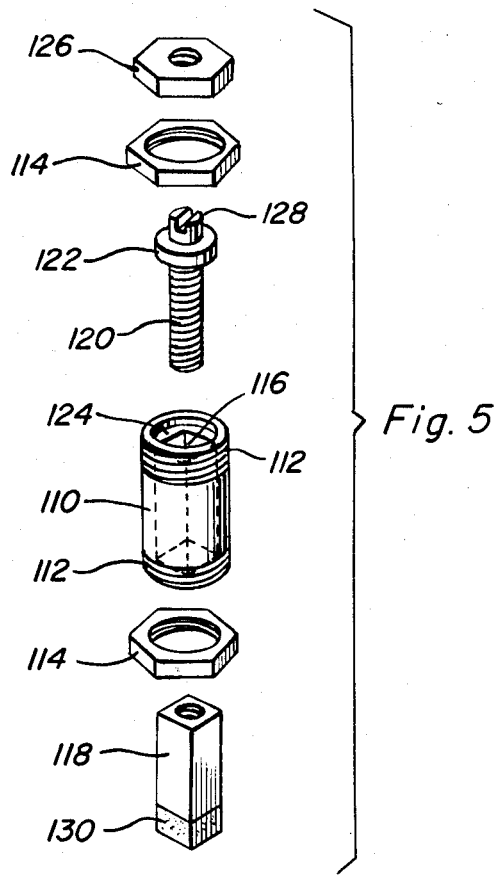
FIG. 5 is an exploded perspective view of the ankle stop of FIG. 4.

An alternative embodiment of ankle stop 20' is shown in FIGS. 4 and 5 which includes a tube 110 having externally threaded end portions 112 for receiving hexagonal nuts 114. The tube 110 extends through the forward portion of the leg member 12 with the nuts 114 received in recesses in the upper and lower surfaces of the forward portion of the leg member. The tube 110 has a substantial internal portion of generally square cross section designated by numeral 116 for slidably and non-rotatably receiving a square-shaped tube 118 having internal threads for threadedly engaging an externally threaded rod member 120. The rod member 120 has a flange 122 of cylindrical configuration integral therewith adjacent the upper end thereof which is rotatably journalled on a shoulder 124 in the upper end of tube 110 and a flanged retaining nut 126 is threaded on the upper threaded end 112 of tube 110 to rotatably retain the flange 122 on the rod member 120 on the shoulder 124. Rotation of the rod member 120 will adjust the position of the square-shaped tube 118 in the tube 110 with the flanged nut 126 also enabling the threaded rod member 120 to be locked in rotatably adjusted position for locking the adjustment of the ankle stop 20'. The upper end of the threaded rod member 118 includes a transverse kerf 128 to receive a screwdriver or similar tool in order to rotatably adjust the rod member 120. The lower end of the square tube 118 has a cushioning tip 130 of rubber or similar material to cushion engagement with the upper surface of the foot member 16. This structure enables adjustment in the forward pivotal movement of the leg member in relation to the foot member in order to compensate for shoes having different heel heights and enable the ankle joint to more closely resemble the movement of a human ankle joint.

A simplified form of the invention may include the omission of the lateral movement joint and its associated structure with the foot member 16 being directly and rigidly connected with the rocker member 44.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An ankle joint for connecting an artificial foot member to an artificial leg member comprising an inverted cup-shaped member attached to the lower end of the leg member and including a longitudinally extending arcuately curved, downwardly facing lower surface, said arcuately curved surface being transversely straight, and a correspondingly-shaped upwardly facing upper surface, a rocker member connected to the foot member and having an arcuate longitudinal surface facing upwardly, said upwardly facing arcuate surface being transversely straight and engaging the correspondingly-shaped downwardly facing surface on the inverted cup-shaped member and bolt means extending through the rocker member and inverted cup-shaped member for connecting said members together, at least one of said inverted cup-shaped member and rocker member having a longitudinally extending slot therein to enable relative pivotal movement between the rocker member and cup-shaped member and between the foot member and leg member about a transverse axis paralleling the transverse straight surfaces and disposed below the transverse straight surface, said leg member including a cavity communicating with the lower end thereof, said bolt means extending upwardly in said cavity above said inverted cup-shaped member, a resilient member mounted on the upper end portion of the bolt means within the cavity for engaging the peripheral walls of the cavity to limit and cushion relative movement between the foot member and the leg member, said arcuate slot being formed in said inverted cup-shaped member, and an overlying cup-shaped member having a downwardly facing longitudinal arcuate surface which is transversely straight corresponding with and slidingly engaging the upwardly facing longitudinally arcuate, transversely straight upwardly facing surface on the inverted cup-shaped member, said inverted cup-shaped member having parallel sidewalls perpendicular with respect to the longitudinally arcuate surface, said rocker member including parallel sidewalls perpendicular to the arcuate longitudinal surface with the sidewalls of the inverted cup-shaped member telescoping downwardly over the sidewalls of the rocker member in close relation to prevent relative pivotal movement of the rocker member and inverted cup-shaped member about a vertical axis defined by the bolt means thereby retaining the foot member properly oriented in a front to rear aspect with respect to the leg member.

2. The structure as defined in claim 1 wherein said rocker member includes a forwardly and rearwardly extending pivot shaft coincidental with the bottom of the rocker member, said foot member including a recess in the upper surface thereof receiving the lower portion of the rocker member, the forward and rearward portions of the recess including a groove receiving the pivot shafts on the rocker member to form a front to rear pivot axis between the foot member and rocker member, said bolt means including a lateral movement joint in the form of a front to rear pivot axis in alignment with the axis defined by the pivot shafts thereby enabling lateral pivotal movement of the foot member with respect to the leg member about a front to rear axis to enable the foot member to incline laterally when the foot is engaged with an inclined supporting surface.

3. The structure as defined in claim 2 wherein said grooves are each provided with a lining of non-metallic material to cushion the pivot shafts and frictionally engage the pivot shafts to avoid free lateral swinging movement of the foot member about a longitudinal axis.

4. The structure as defined in claim 2 together with an adjustable stop member mounted in the forward lower portion of the leg member and including an abutment engageable by the upper surface of the foot member in spaced relation to the transverse axis of pivotal movement.

5. The structure as defined in claim 4 wherein said adjustable stop member includes a threaded bolt having a head at the lower end defining the abutment with the threaded bolt extending through a portion of the leg member, nuts on the bolt engaging the upper and lower surface of the leg member in order to vary the position of the head of the bolt.

6. The structure as defined in claim 6 wherein said abutment is in the form of a resilient lower tip on a vertically slidable, non-rotatable polygonal shaft, and threaded connection means between the non-rotatable shaft and said leg member.

7. The structure as defined in claim 6 wherein said connection means between the foot member and the non-rotative member includes a rotatable threaded member threadedly engaged with the non-rotatable member, said rotatable threaded member including a flange captively supported from a support sleeve in the foot member to enable rotation thereof but preventing longitudinal movement thereof, the upper end of the rotatable threaded member including tool engaging means to enable rotation thereof and adjustment of the abutment to vary the position of the foot member when it engages the tip.

8. An ankle joint for connecting an artificial foot member to an artificial leg member comprising an inverted cup-shaped member attached to the lower end of the leg member and including a longitudinally extending arcuately curved, downwardly facing lower surface, said arcuately curved surface being transversely straight, and a correspondingly-shaped upwardly facing upper surface, a rocker member connected to the foot member and having an arcuate longitudinal surface facing upwardly, said upwardly facing arcuate surface being transversely straight and engaging the correspondingly-shaped downwardly facing surface on the inverted cup-shaped member and bolt means extending through the rocker member and inverted cup-shaped member for connecting said members together, at least one of said inverted cup-shaped member and rocker member having a longitudinally extending slot therein to enable relative pivotal movement between the rocker member and cup-shaped member and between the foot member and leg member about a transverse axis paralleling the transverse straight surfaces and disposed below the transverse straight surfaces, and an adjustable stop member mounted in the forward lower portion of the leg member and including an abutment engageable by the upper surface of the foot member in spaced relation to the transverse axis of pivotal movement, said abutment being in the form of a resilient lower tip on a vertically slidable, non-rotatable polygonal shaft, and threaded connection means between the non-rotatable shaft and said leg member.

9. An adjustable stop for limiting articulate movement between an artificial leg member an an artificial foot member in which the leg member includes a forwardly extending lower portion overlying an upper surface of a forwardly extending portion of the foot member, said adjustable stop including a threaded member mounted on the leg member and including a lower end engageable with the upper surface of the foot member, said threaded member including an internally threaded tube of polygonal cross-sectional configuration slidably mounted in a correspondingly shaped recess in the leg member and an externally threaded member threaded into the internally threaded member with the externally threaded member being rotatably and non-longitudinally movably mounted on the leg member for adjusting the non-rotatable member, the lower end of the non-rotatable member including a resilient tip forming an abutment for engagement with the upper surface of the foot member.

* * * * *